(12) United States Patent
Gedebou

(10) Patent No.: US 6,896,689 B2
(45) Date of Patent: May 24, 2005

(54) TISSUE EXPANDER, SYSTEM AND METHOD

(76) Inventor: Tewodros Gedebou, 8614 Burton Way, Apartment #205, Los Angeles, CA (US) 90048

( * ) Notice: Subject to any disclaimer, the term of this patent is extended or adjusted under 35 U.S.C. 154(b) by 210 days.

(21) Appl. No.: 10/352,473

(22) Filed: Jan. 28, 2003

(65) Prior Publication Data

US 2004/0147953 A1 Jul. 29, 2004

(51) Int. Cl.$^7$ ............................................. A61M 29/00
(52) U.S. Cl. ....................................... 606/191; 128/898
(58) Field of Search ................................ 606/191, 194, 606/198, 201, 202, 203; 600/490, 499; 623/7, 8

(56) References Cited

U.S. PATENT DOCUMENTS

| | | |
|---|---|---|
| 4,574,780 A | 3/1986 | Manders |
| 4,662,357 A | 5/1987 | Pierce et al. |
| 4,671,255 A | 6/1987 | Dubrul et al. |
| 4,685,447 A | 8/1987 | Iversen et al. |
| 4,798,205 A | 1/1989 | Bonomo et al. |
| 4,800,901 A | 1/1989 | Rosenberg |
| 4,899,764 A | 2/1990 | Gauger et al. |
| 4,950,292 A | 8/1990 | Audretsch |
| 4,955,395 A | 9/1990 | Manders |
| 5,033,481 A | 7/1991 | Heyler, III |
| 5,066,303 A | 11/1991 | Bark et al. |
| 5,074,878 A | 12/1991 | Bark et al. |
| 5,092,348 A | 3/1992 | Dubrul et al. |
| 5,141,508 A | 8/1992 | Bark et al. |
| 5,146,933 A * | 9/1992 | Boyd .......................... 128/899 |
| 5,158,571 A | 10/1992 | Picha |
| 5,496,368 A | 3/1996 | Wiese |
| 5,549,672 A * | 8/1996 | Maddock et al. ............... 623/8 |
| 5,571,179 A | 11/1996 | Manders et al. |
| 5,630,843 A | 5/1997 | Rosenberg |
| 5,964,803 A | 10/1999 | Iversen et al. |
| 5,984,942 A | 11/1999 | Alden et al. |
| 6,071,309 A | 6/2000 | Knowlton |
| 6,120,437 A | 9/2000 | Yoon et al. |
| 6,206,930 B1 | 3/2001 | Burg et al. |
| 6,228,116 B1 | 5/2001 | Ledergerber |
| 6,432,081 B1 | 8/2002 | Atala |
| 6,666,893 B2 * | 12/2003 | Burg et al. ..................... 623/8 |
| 2001/0004709 A1 | 6/2001 | Dubrul |
| 2001/0010024 A1 | 7/2001 | Ledergerber |
| 2001/0032019 A1 | 10/2001 | Van Dyke et al. |
| 2002/0010514 A1 | 1/2002 | Burg et al. |

* cited by examiner

*Primary Examiner*—Kevin T. Truong
(74) *Attorney, Agent, or Firm*—Stetina Brunda Garred & Brucker

(57) ABSTRACT

Non-fluidized tissue expanders, tissue expander systems, and methods of expanding tissue are disclosed. The tissue expanders, systems, methods of the present invention incorporate an expandable encapsulated body mass implantable within the patient and operative to selectively expand to promote growth of an enlarged area of skin and subcutaneous tissue. Such tissue expansion is accomplished utilizing internal one or more distraction mechanisms disposed within the tissue expanders that are operative to expand by mechanical or electro-mechanical means. The present invention omits any type of inflatable body requiring the injection of fluids to effectuate expansion of the tissue expander.

4 Claims, 4 Drawing Sheets

TISSUE EXPANDER, SYSTEM AND METHOD

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention is directed to improved tissue expanders, tissue expander systems, and methods for expanding tissue. More particularly, the present invention is directed to non-fluidized tissue expanders and systems that are operative to selectively and controllably expand in a completely self-contained environment without requiring any type of inflation means.

In this regard, tissue expanders are well-known in the art. Exemplary of such tissue expanders include those disclosed in U.S. Pat. No. 5,066,303 to Bark et al.; U.S. Pat. No. 4,671,255 to Dubrul et al.; U.S. Pat. No. 4,662,357 to Pierce et al.; U.S. Pat. No. 4,685,447 to Iversen et al.; and U.S. Pat. No. 4,899,764 to Gauger et al., the teachings of all of which are expressly incorporated by reference.

Essentially, tissue expanders of the prior art comprise an inflatable body, having an inflation valve or button connected thereto, the latter typically being formed upon the inflatable body itself, as described in U.S. Pat. Nos. 4,671, 255 and 5,066,303, on one hand, or located remotely and connected to the inflatable body by means of an elongated conduit, as disclosed in U.S. Pat. Nos. 4,899,764 and 4,685, 447.

In either embodiment, the inflatable body of the tissue expander is placed subcutaneously within the locus where tissue is to be expanded. The inflation valve is likewise positioned or implanted subcutaneously to allow gradual introduction of fluid, which is typically saline, into the inflation body by injection. After gradual inflation at pre-determined intervals, the skin and subcutaneous tissues overlying the expander are consequently caused to expand in response to the pressure exerted upon such tissues by the inflatable body as solution is gradually introduced there into.

After gradual inflation at pre-determined intervals, which may extend over weeks or months, the skin and subcutaneous tissue will expand to the point where further medical procedures can be performed, such as the permanent implantation of a prosthesis, plastic and reconstructive surgery, or for use of the skin and subcutaneous tissue for use in some other part of the body.

Despite their widespread applicability and extensive utilization, however, most tissue expanders suffer from numerous drawbacks. In this regard, virtually all tissue expanders rely upon an inflatable body requiring incremental quantities of fluid to be introduced therein to thus cause the desired expansion. Because virtually all fluids introduced into inflatable-type tissue expanders must necessarily be administered by injection, the procedure by which such fluids are introduced can be painful and increase the risk of an inadvertent needle stick experience. With respect to the latter, it is well-known that such an experience can lead to the transmission of blood borne diseases, such as hepatitis and HIV.

Moreover, it is well-known that the use of hypodermic needles to deliver fluid frequently results in the inadvertent puncture of the inflatable body of the expander. As a consequence, a leakage is formed in the inflatable body that requires surgical replacement of the tissue expander, which further results in additional surgery, patient discomfort, expense, and increased healing time.

Along these lines, because the delivery of fluid into tissue expanders requires the use of hypodermic needles, such procedure must necessarily be performed by skilled health care workers, which adds significantly to the expense associated with utilizing tissue expanders, as well as inconveniences patients who must routinely make office visits and the like in order to insure proper tissue expansion. Indeed, it is a recognized problem with conventional tissue expanders when attempts we made to expand the inflatable body as rapidly as practical to thus minimize the number of injections (and hence office visits) to be administered. Such practice, however, frequently results in the tissue expander being expanded too rapidly, which can cause substantial pain for the patient and damage the skin and subcutaneous tissues sought to be increased.

As such, there is a substantial need in the art for a tissue expander that can effectively and efficiently expand over time so as to generate an enlarged area of overlying tissue that does not rely upon the infusion of fluids into an inflatable body. More specifically, there is a need for a tissue expander that completely eliminates the need to administer injections or otherwise place the patient and health care worker at increased risk of a needle stick experience in order to introduce fluids to cause expansion of the tissue expander, as per conventional prior art tissue expanders. There is yet further a need in the art for a tissue expander that can be designed according to any of a variety of configurations to thus attain selective and controllable tissue expansion in a manner far superior than prior art tissue expanders. Still further there is a need in the art for such a tissue expander that is of simple construction, may be readily fabricated from existing materials utilizing existing technology, can be utilized for a wide variety of tissue expansion applications, is safe and of relative low cost, can be operated in a very simple manner that may not require procedures involving skilled health care workers, and can be readily implemented for use in virtually all types of procedures requiring tissue expansion.

BRIEF SUMMARY OF THE INVENTION

The present invention specifically addresses and alleviates the above-identified deficiencies in the art. In this regard, the present invention comprises a tissue expandes, tissue expander systems and methods of tissue expansion that are operative to facilitate the growth and enlargement of skin and subcutaneous tissue, as per conventional prior art tissue expanders, but omit any type of fluid-filled, inflatable body requiring the repetitious input of fluids via injection to effectuate the desired expansion of the device.

According to a preferred embodiment, the tissue expander of the present invention comprises an encapsulated body mass implantable within the body and operative to selectively expand over time. The encapsulated body mass will preferably be formed from a covering of silicone rubber or any other type of silicone or bio-compatible elastomer well-known in the art, including those silicone-based materials utilized with conventional tissue expander devices.

Disposed within the encapsulated body is an adjustable distraction mechanism that is operatively transitional between a first retracted configuration, wherein such distraction mechanism conserves volume within the encapsulated body mass to thus enable the tissue expander to be selectively implanted beneath the skin and subcutaneous tissue, and an operative configuration, wherein the distraction exerts an outwardly expansive force operative to increase the surface area of the exterior of the encapsulated body. To accomplish that end, the distraction mechanism as incorporated within the tissue expander of the present invention is entirely self contained within the encapsulated body mass and is capable of being externally manipulated or controlled via an actuator disposed within the body mass and coupled to the distraction mechanism such that the rate of expansion within the encapsulated body mass attains a desired rate of expansion.

The distraction incorporated within the encapsulated body mass may take any of a variety of means known in the art, including both mechanical and electro-mechanical mechanisms. Such mechanical embodiments can comprise a simple mechanical jack whereby a ratchet-type actuator is operative to cause an upwardly-extending jack to impart an upwardly-expansive force about the encapsulated body mass to thus increase the size and surface area of the tissue expander. Alternatively, the distraction can comprise a spring-loaded system that is operative to selectively exert an outwardly-expansive force to the encapsulated body mass that may be selectively controlled via an internal ratchet, the latter being controllable via external manipulation of the implanted encapsulated body mass. According to another embodiment, the distraction mechanism will accomplish expansion via hydraulic means whereby an internal reservoir of fluid will be activated via a valve and pump actuator, which may be activated via the application of external pressure, to exert a piston-driven, outwardly-expansive force against the encapsulated body mass. In yet another embodiment, selective expansion of the encapsulated body mass may be effectuated through selectively arranged rare earth magnets that are operative to repel one another via select orientation of the magnets' poles relative one another, to thus cause the magnets to exert an outwardly-expansive force within the encapsulated body member.

It is further contemplated that such distraction mechanism may rely upon electro-mechanical means, including the use of a small implantable, battery-powered motor disposed within the encapsulated body mass that is operative to impart an outwardly-expansive force, and hence a volumetric expansion within the encapsulated body mass, upon the receipt of signals generated from an external source. Such motor-driven system may comprise a simple solenoid-type mechanism that is operative to impart an outwardly-expansive force upon select application of a current to the solenoid, as is well-known in the art.

In any of the aforementioned embodiments, however, the encapsulated body mass will be caused to selectively expand to a desired shape and/or size over a desired length of time without requiring the inflation of an inflatable body using an externally delivered fluid or any other system whereby an expansive material needs to be injected into the expander. In this regard, the tissue expanders of the present invention are operative to impart more effective expansion by controlling the direction of the expansion in such a manner that allows the expanded tissue to drape over the area to be replaced, which has not heretofore been available via the use of prior art tissue expanders.

Once the desired degree of expansion has been attained, the tissue expanders and systems of the present invention are operative to transition back to its original, neutral non-operative state to thus enable the expander to be removed from the body, as per conventional tissue expander devices. In this regard, the distraction mechanism will be operative to transition back to its neutral configuration, to thus minimize the external surface area of the tissue expander. Along these lines, it is contemplated that the tissue expanders of the present invention will be capable of identically mimicing conventional tissue expander devices whereby the same are drained to assume a deflated state and thereafter removed. Advantageously, however, at no time are fluids ever introduced into the tissue expander of the present invention and further, because the degree of tissue expansion imparted by the tissue expanders of the present invention are not dependent upon incremental increases in fluid which must necessarily imparted by a health care worker, the tissue expanders, tissue expander systems, and methods of the present invention attain a far more uniform expansion of tissue, are substantially less painful, less traumatic, require minimal skill to manipulate (i.e., can be operated directly by the patient), have a much lesser risk of becoming inadvertently deflated, can expand tissue more rapidly, and pose a substantially lesser degree of risk than the tissue expanders and methods of the prior art.

BRIEF DESCRIPTION OF THE DRAWINGS

These as well as other features of the present invention will become more apparent upon reference to the drawings wherein.

DETAILED DESCRIPTION OF THE INVENTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood however, that the same or equivalent functions and sequences may be accomplished by different embodiments and that they are also intended to be encompassed within the scope of the invention.

Figure 1:
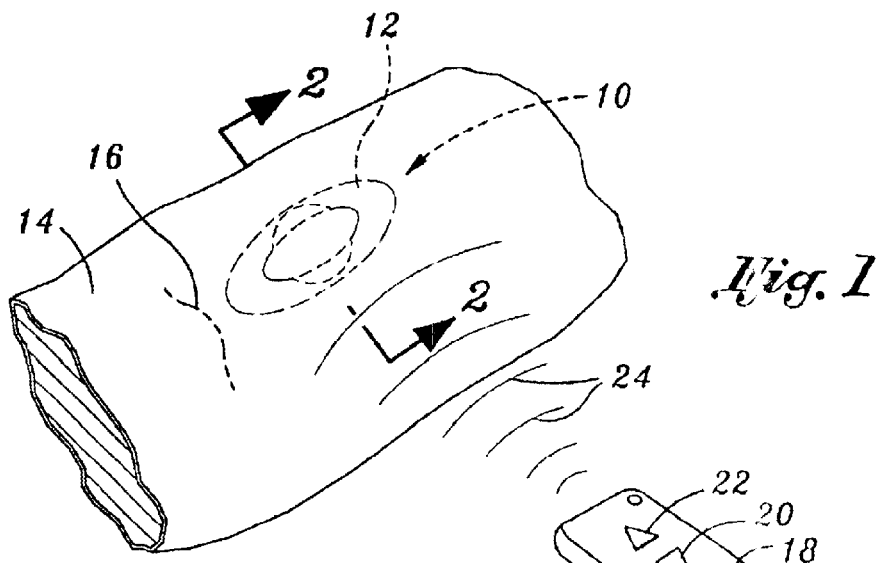
FIG. 1 is a perspective view of a tissue expansion system constructed in accordance with a preferred embodiment of the present invention, the tissue expander of which is shown implanted underneath layers of skin and subcutaneous tissue.

Referring now to the drawings, and initially to FIG. 1, there is illustrated a tissue expander 10 for use in facilitating the growth of skin and subcutaneous tissue, as may be desired for a wide variety of medical procedures. As illustrated, the device 10 comprises an implantable encapsulated body mass 12 that is designed to be positioned beneath the skin 14 of a patient through incision 16. In this regard, it is contemplated that the tissue expander 10 of the present invention will be sized and adapted for surgical implantation as per conventional tissue expander devices well-known and extensively utilized in the art, and may further be adapted to be implanted beneath muscle as may be desired for certain applications.

Unlike such prior art devices, however, the tissue expander 10 of the present invention is configured to provide an outwardly-expansive pressure, and hence volumetric expansion and increase in external surface area, without requiring fluids to be injected through the skin, whether it be directly into the tissue expander itself or a remotely-positioned valve fluidly connected to the tissue expander, as is typical with virtually all tissue expanders of the prior art.

To accomplish that end, the tissue expanders 10 of the present invention are specifically designed to completely encapsulate a distraction mechanism, discussed more fully below, that is operative to impart an outwardly-expansive force to thus cause the tissue expander 10 to expand. Advantageously, the distraction mechanism will be configured such that the same will be selectively and controllably operable via forces and/or signals that are applied either externally to or externally from the patient. As such, the tissue expanders of the present invention completely eliminate all risks and drawbacks associated with prior art tissue expanders requiring the use of hypodermic needles and the like to inflate an inflatable body or the like.

Figure 2:
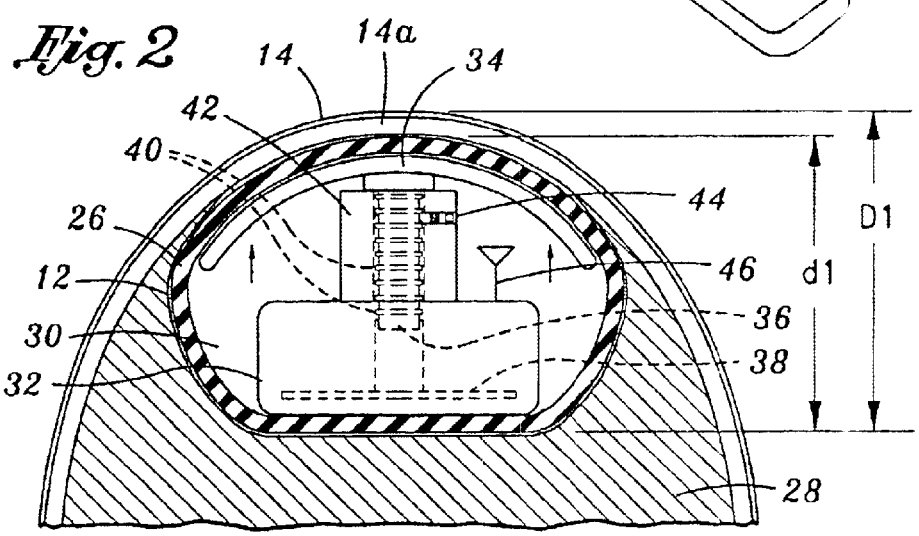
FIG. 2 is a cross-section view taken along line 2—2 of FIG. 1, such picture depicting an encapsulated body mass of the tissue expander housing a distraction mechanism therein, the latter shown assuming a retracted, compact configuration conserving volume within the encapsulated body mass.
Figure 3:
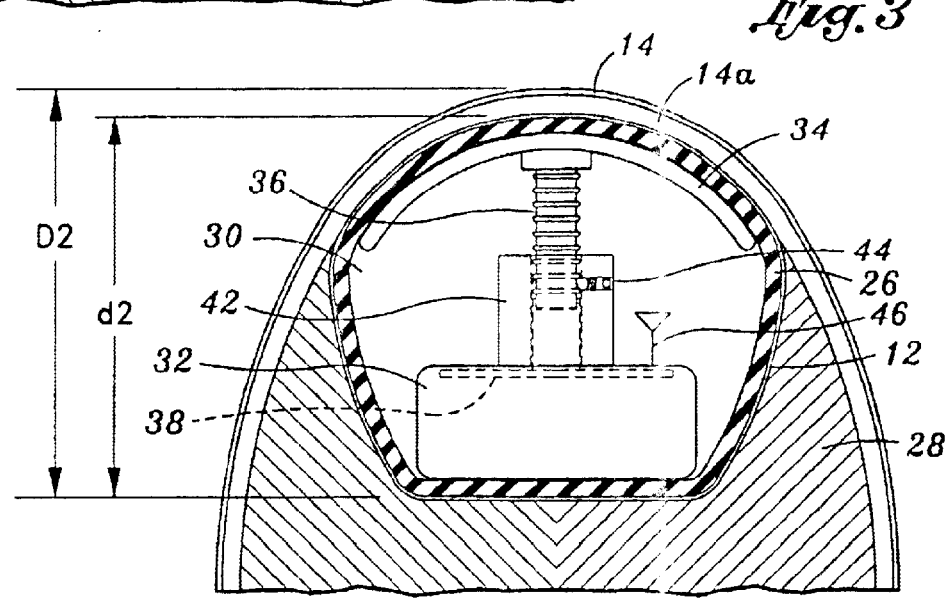
FIG. 3 is the cross-sectional view of FIG. 2 showing the distraction mechanism assuming an operative configuration wherein the encapsulated body mass is caused to expand outwardly and increase in volume and external surface area.

With respect to the embodiment depicted in FIGS. 1–3, the same is directed to a tissue expander system utilizing a remote control mechanism 18 operative to send signals 24 to the tissue expander 10 to thus cause the same to selectively expand over time. In this regard, remote control 18 will be provided with mechanisms 20, 22 that are operative to selectively control the degree of expansion and/or contraction of the body mass 12 thereof to a degree as may be desired.

Referring now to FIGS. 2 and 3, initially to FIG. 2, there is shown the encapsulated body mass 12 as implanted underneath skin 14 and subcutaneous tissue layer 14a and operative to effectuate the expansion thereof. In this respect, body mass 12 will be implanted within tissue 28 as per conventional tissue expander devices. The body mass 12 will comprise an outer covering 26 formed from an elastic material, which may take any of a variety of bio-compatible materials known in the art, such as silicone rubber and the like. The covering 26 defines an internal cavity 30, which will assume a neutral or implantable configuration, as shown in FIG. 2, wherein the volume of the internal cavity 30 is minimized. In this respect, such reduced size facilitates the ability of the expandable body mass 12 to be surgically implanted into position.

Disposed within the cavity 30 is a distraction mechanism 32, which is operative to cause the outer covering 26 to expand outwardly toward skin and subcutaneous layers 14, 14a over a desired duration of time. To achieve that end, distraction mechanism 32 as shown will be provided with an outwardly extending compression piece 34 that is driven upwardly by piston 36, the latter being formed upon base 38 and having a plurality of ribs 40 formed thereon, the latter providing a mechanism for selectively controlling the degree of expansion imparted by compression piece 34. The distraction mechanism 32 is further provided with an actuator 46 which is operative to receive signals 24 from remote control 18, as shown in FIG. 1. In this respect, it is contemplated that the signals 24 received by actuator 46 will be transmitted to the distraction mechanism to thus cause piston 36 to advance upwardly as shown.

As will be readily appreciated in the art, to effectuate such expansion, it is contemplated that distraction mechanism 32 may take any of a variety of electro-mechanical mechanisms well-known in the art. In this respect, it is contemplated that distraction mechanism 32 may be a motor-driven mechanism, preferably is battery powered, that can cause piston 36 to extend upwardly at a desired rate. It is further contemplated that control mechanisms, such as latch 44, will be provided to engage with ribs 40 at select intervals such that the upward expansion caused by compression piece 34 progresses at a selectively controllable rate. In the specific embodiment shown, such distraction mechanism 32 may take the form of a conventional solenoid system that is operative to cause piston 36 to advance upwardly upon application of a current. As will be appreciated by one of ordinary skill, however, it is contemplated that a wide variety of other types of electro-mechanical mechanisms may be readily deployed for use in the practice of the present invention.

Irrespective of the embodiment of the distraction mechanism 32 utilized, eventually the distraction mechanism will cause the encapsulated body mass 12 to increase in external surface area, as illustrated in FIG. 3. In this regard, the upward application of force by compression piece 34 against layer 26 causes skin 14 and subcutaneous tissue 14a to expand. To illustrate this point, FIG. 2 depicts the distraction mechanism assuming a first neutral configuration wherein the distraction mechanism is maintained in a retracted, compact configuration such that a minimal baseline amount of pressure is applied upwardly against layer 26. Such conserved space and volume is represented by d1, which in turn imparts a limited degree of pressure upwardly against skin and subcutaneous tissue layers 14, 14a, as represented by D1.

As the distraction mechanism 32 applies an outwardly-expansive force, as accomplished through the upward-extension of piston 36 with compression piece 34 formed thereon, the external size of the body mass 12 is caused to increase, thus causing an expanded surface area, as illustrated by the spacing d2. Such increased surface area consequently causes skin and subcutaneous tissue 14, 14a to stretch and expand over a greater area, as represented in the distance D2.

Advantageously, given the orientation of distraction mechanism 32 within elastomeric covering 26, encapsulated body mass 12 will selectively expand in volume and external surface area to thus produce a greater area about which skin and subcutaneous tissue 14, 14a will extend. In this regard, the mechanism by which skin and subcutaneous tissue 14, 14a expand identically mimics that accomplished by conventional tissue expanders utilizing fluid-based systems whereby fluid is introduced within the cavity of an inflatable bladder or other like member. Unlike such prior art devices, however, fluid need not be introduced within the internal cavity 30 of the encapsulated body mass 12, which thus dispenses with the need for the use of any type of hypodermic needle or other like procedure for introducing fluids therein.

Figure 4:
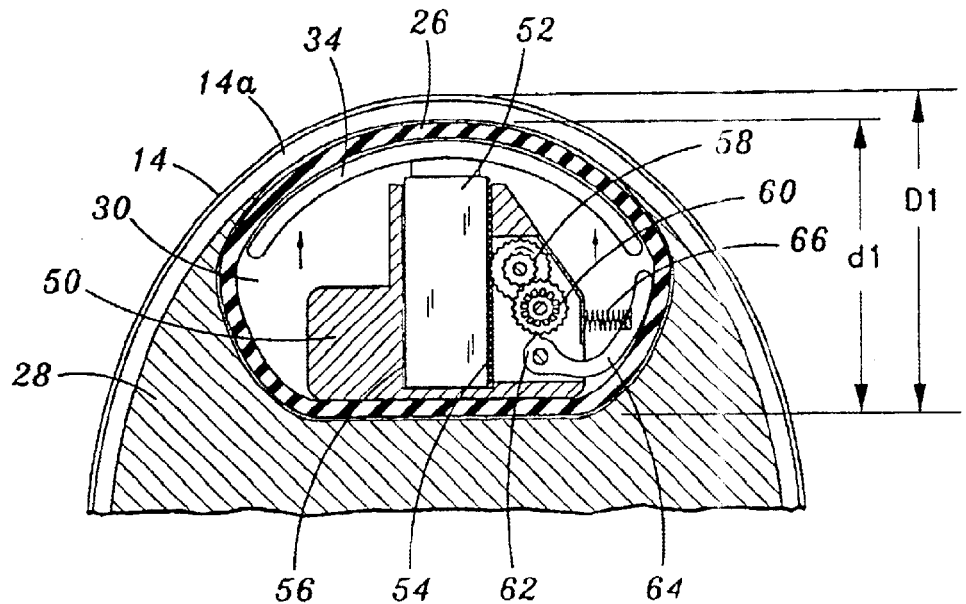
FIG. 4 is a cross-sectional view of a tissue expander constructed in accordance with another preferred embodiment of the present invention, the tissue expander being shown assuming a space-conserving configuration with the distraction mechanism thereof within the encapsulated body mass assuming a retracted configuration.
Figure 5:
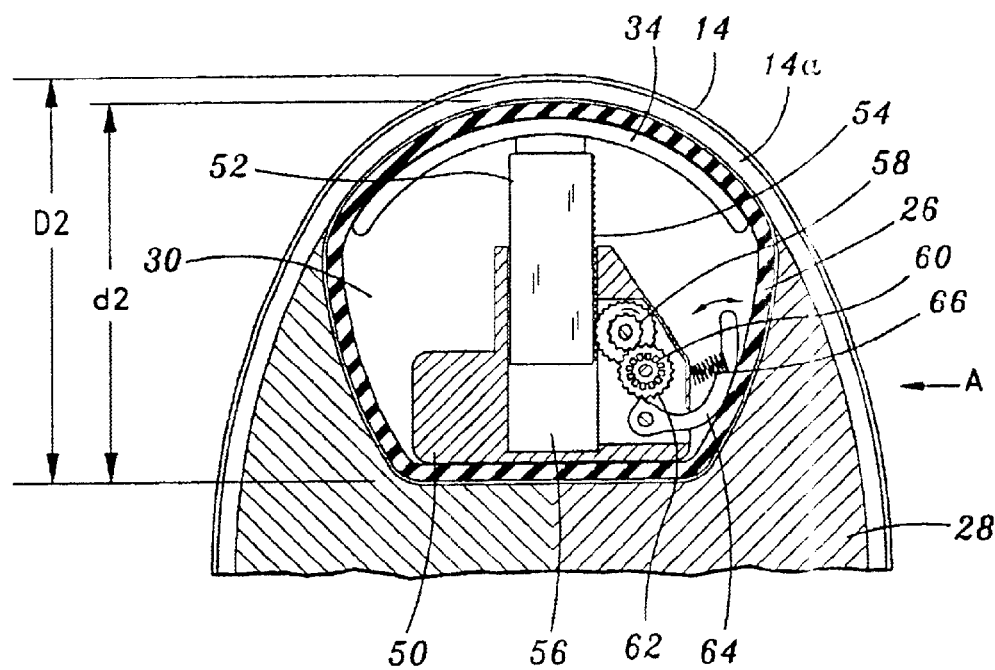
FIG. 5 is a cross-sectional view of the tissue expander of FIG. 6 shown assuming an expanded, operative configuration wherein the distraction mechanism is operative to exert an outward pressure upon the encapsulated body mass.

Referring now to FIGS. 4 and 5, and initially to FIG. 4, there is illustrated the tissue expander of the present invention incorporating a purely mechanical distraction mechanism 50 for use in effectuating the expansion of skin and subcutaneous tissue 14, 14a. As illustrated, the distraction mechanism 50 is shown in a first neutral configuration, illustrated in FIG. 4, whereby the same assumes a space-efficient, compact shape that minimizes volume within the cavity 30 of the encapsulated body mass 12. As discussed above with respect to the embodiment depicted in FIGS. 1–3, the distraction mechanism 50 will be operative to impart a minimal, baseline amount of upward pressure against covering 26, and hence skin and subcutaneous tissue 14, 14a at the time of implantation. As such, the amount of expansion, represented by d1, D1 is minimized.

In use, the distraction mechanism 50 will be operative to transition from the neutral configuration, depicted in FIG. 4, to an operative configuration whereby compression piece 34 is operative to exert an upwardly-expansive force against covering 26, and ultimately skin and subcutaneous tissue layers 14, 14a to thus facilitate the growth thereof. In the embodiment shown, the distraction mechanism 50 deploys a simple mechanical jack whereby an upwardly-extending piston 52, having a plurality of teeth 54 arranged along the edge thereof, is received within socket 56 formed within the distraction mechanism 50 and operative to extend therefrom.

The teeth 54 of piston 52 are operatively coupled to a first ratchet wheel 58, the latter being operatively coupled to a second ratchet wheel 60, which in turn is operatively coupled to ratchet lever 64 having a toothed member 62 formed thereon for sequentially causing ratchet wheels 58, 60 to sequentially turn, and thus cause the piston 52 to advance upwardly, as illustrated in FIG. 5. Such upward expansion of piston, and hence compression piece 34, consequently causes in increase in external surface area of the body mass 12 as illustrated in the increased dimensions of d2, D2, the latter providing the greater surface area about which layers 14, 14a will overlay.

To facilitate the ability of the encapsulated body mass, and more particularly the distraction mechanism 50 encapsulated therein, to effectuate the desired increase in size and surface area, the ratchet lever 64 will be operative to function as an actuator that can be selectively and controllably actuated via the application of an external pressure applied in the direction indicated by the letter "A". As will be readily appreciated by one skilled in the art, by merely applying an external force outside of layers skin 14, 14a, the tissue expander of the present invention will be operative to expand without having to inject or otherwise penetrate through the layers of skin sought to be expanded. Advantageously such method of expansion is substantially less painful, poses significantly less risk, and can provide for much more precise tissue expansion than prior art tissue expanders utilizing fluid inflation means.

To further facilitate the ability of the distraction mechanism 50 to impart a desired degree of expansive force, ratchet lever 64 will preferably be coupled to a spring element 66 that enables the ratchet lever 64 to be easily manipulated and capable of rendering a precise incremental increase or decrease in expansive pressure applied by the distraction mechanism, via compression piece 34 about layer 26.

As will be readily appreciated by those skilled in the art, although depicted in FIGS. 4 and 5 as a jack, the distraction mechanism element of the present invention should be deemed to encompass any type of mechanical mechanism capable of selectively and controllably applying an outwardly-expansive force operative to increase the surface area of a tissue expander while remaining self-contained therein.

Although not shown, such distraction mechanism may comprise a spring-loaded mechanism whereby a spring applies an upwardly-expansive force, as per piston elements 36 and 52 of FIGS. 2 and 3, on one hand, and FIGS. 4 and 5, on the other hand. According to such embodiment, it is contemplated that such spring-loaded device will be controlled as per the embodiment depicted in FIGS. 4 and 5 whereby a ratchet arm or other like member will selectively control the degree of compression of the spring and controllably allow the same to impart a desired degree of outwardly-expanding pressure.

Alternatively, the distraction mechanism may take the form of a hydraulic lift whereby a hydraulically-driven piston is caused to exert an outwardly-expansive force, as selectively controlled by an actuator pump and valve mechanism coupled therewith, the latter being readily known to those skilled in the art.

In a still further embodiment, such distraction mechanism may take the form of two or more earth magnets that are selectively positioned within the encapsulated body mass and coupled to an actuator, operative to control the relative position of said magnets. According to such embodiment, the actuator will be operative to place the magnets in relative proximity one another such that the same are repelled due to the orientation of like magnetic poles, the principles of which are easily understood in the art. The repelling force between the magnets will be operative to impart an outwardly-expansive force to thus ultimately cause an increase in surface area of the encapsulated body mass.

It will therefore be appreciated that a wide variety of mechanisms, both mechanical and electro-mechanical, may be readily incorporated for use as the distraction mechanism of the present invention. In all embodiments, however, such distraction mechanism must be completely self contained and capable of effectuating systematic and controllable expansion of the tissue expander without requiring any type of subcutaneous contact or manipulation, and in particular, any type of hypodermic manipulation requiring the injection of fluids and the like. Along these lines, it is contemplated that the distraction mechanism as incorporated into the expander of the present invention will be capable of being controllably activated via external manipulation, such as the application of external pressure which can be manually applied by the patient or by other mechanical or electro-mechanical means described herein to thus alleviate the need for skilled health care workers to be involved in the tissue expansion procedure.

Bearing the foregoing principles in mind, there is depicted in FIGS. 6–13 multiple embodiments of tissue expanders of the present invention operative to impart a desired degree and orientation of tissue expansion, as may be desired for a particular application. Along these lines, it should be recognized at the outset that the tissue expanders of the present invention may be specifically designed and configured to facilitate not only the growth of skin and subcutaneous tissue, but may also cause such skin and subcutaneous tissue to grow according to a specific orientation or in differential amounts, as is highly desired and warranted for a variety of medical applications. As such, the tissue expanders of the present invention, by allowing the tissue to be expanded according to a variety of orientations, provides for substantially more precise tissue expansion and substantially facilitates the ability for subsequent medical procedures to be optimally performed.

Figure 6:
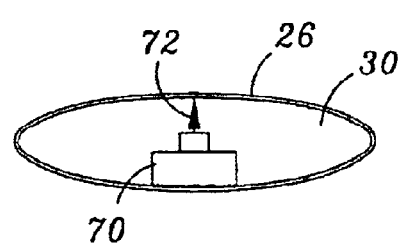
FIG. 6 is a cross-sectional view of a tissue expander constructed according to a preferred embodiment assuming a first neutral, generally oval shape with the distraction mechanism thereof shown assuming a retracted configuration.
Figure 7:
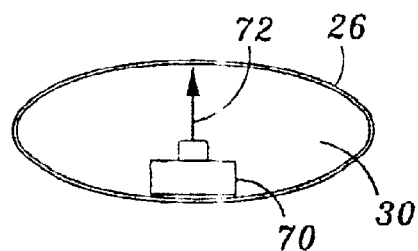
FIG. 7 is a cross-sectional view of the tissue expander of FIG. 6 with the expander shown assuming an operative, expansive configuration.
Figure 8:
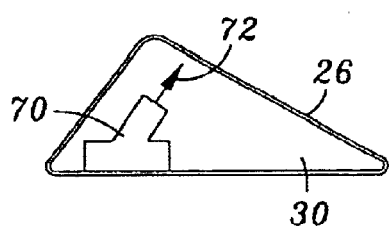
FIG. 8 is a cross-sectional view of a tissue expander constructed in accordance with the preferred embodiment of the present invention shown assuming first a neutral, generally triangular shape.
Figure 9:
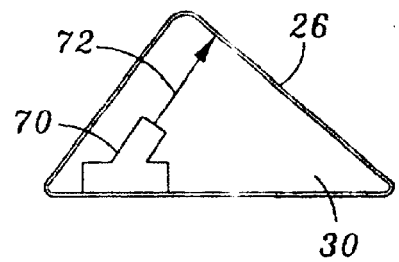
FIG. 9 is a cross-sectional view of the tissue expander of FIG. 8 shown assuming an expanded triangular shape.

Referring now to FIGS. 6 and 7, there is shown an elliptical embodiment of the tissue expander of the present invention shown in a first neutral configuration, depicted in FIG. 6, whereby the outer covering 26 assumes a flattened configuration defining a flattened elliptical interior surface cavity 30. In the expanded configuration depicted in FIG. 7, the elliptical shape is caused to increase in surface area based upon the application of an outwardly-expansive force 72 imparted by distraction mechanism 70. FIGS. 8 and 9 depict a generally triangular embodiment wherein the tissue expander assumes a neutral configuration, depicted in FIG. 7, with the distraction mechanism 70 being disposed at a respective end of the triangular member. In FIG. 9, the outwardly-expansive force 72 imparted the distraction mechanism 70 is operative to cause the triangular-shaped tissue expander to expand, yet do so while possessing a generally triangular shape. As will be appreciated, in order to effectuate the ability of the tissue expander to expand while retaining such shape, it may be necessary to utilize reinforcing materials within covering 26 to thus cause the expander to expand having walls possessing some degree of rigidity.

Figure 10:
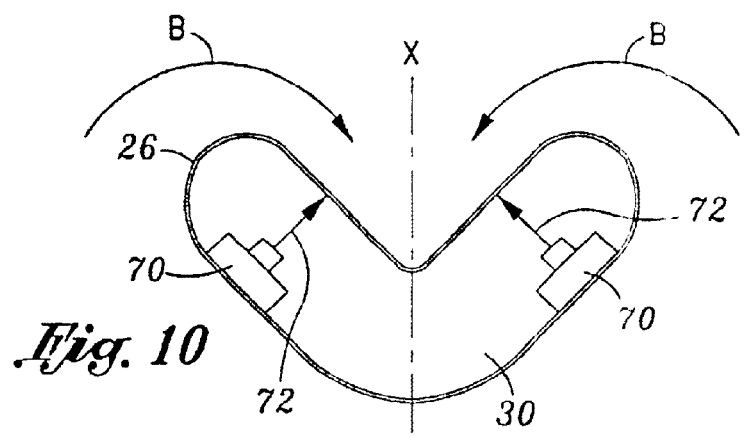
FIG. 10 is a cross-sectional view of a tissue expander constructed in accordance with a preferred embodiment of the present invention showing two distraction mechanism disposed within an encapsulated body mass, the encapsulated body mass shown assuming a neutral, generally V-shaped configuration.
Figure 11:
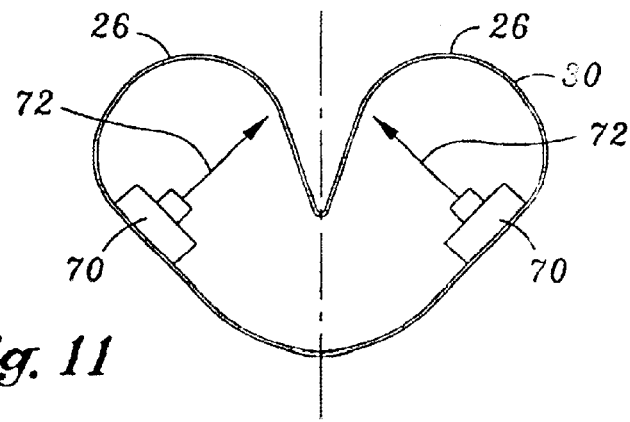
FIG. 11 is a cross-sectional view of the tissue expander of FIG. 10 wherein the distraction mechanisms are shown imparting an inwardly-compressive force within the encapsulated body mass.

Referring now to FIGS. 10 and 11, there is shown a tissue expander operative to facilitate the growth of skin and subcutaneous tissue about a central axis "X". In the embodiment shown, the tissue expander utilizes two distraction mechanisms 70 which each impart an outwardly-expansive pressure 72 causing outer covering 26 to rotate inwardly, as indicated by the direction "B", such that a greater surface area is produced that is biased inwardly toward axis "X", as reflected in FIG. 11. As will be appreciated by those skilled in the art, such embodiment is operative to facilitate the growth of skin and subcutaneous tissue as may be desired to form a closure or otherwise receive a permanent implant and the like. Advantageously, because of the ability of the distraction mechanisms 70 to impart a desired shape and orientation of the tissue expander, a more precise and selectively controlled underlying shape can be formed, to thus promote precise and geometrically controllable means to promote skin and subcutaneous tissue growth, that cannot otherwise be attained utilizing tissue expanders possessing inflatable bodies, chambers, and the like.

Figure 12:
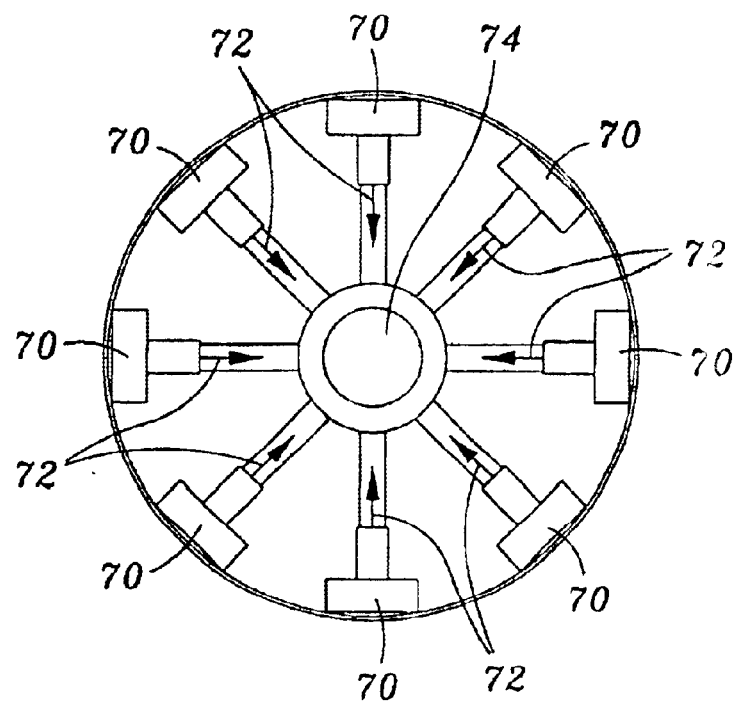
FIG. 12 is a cross-sectional view of the tissue expander constructed in accordance with a preferred embodiment of the present invention shown having an annular configuration with multiple distraction mechanisms formed therein, the tissue expander shown having an expanded configuration defining a first expanded surface area.
Figure 13:
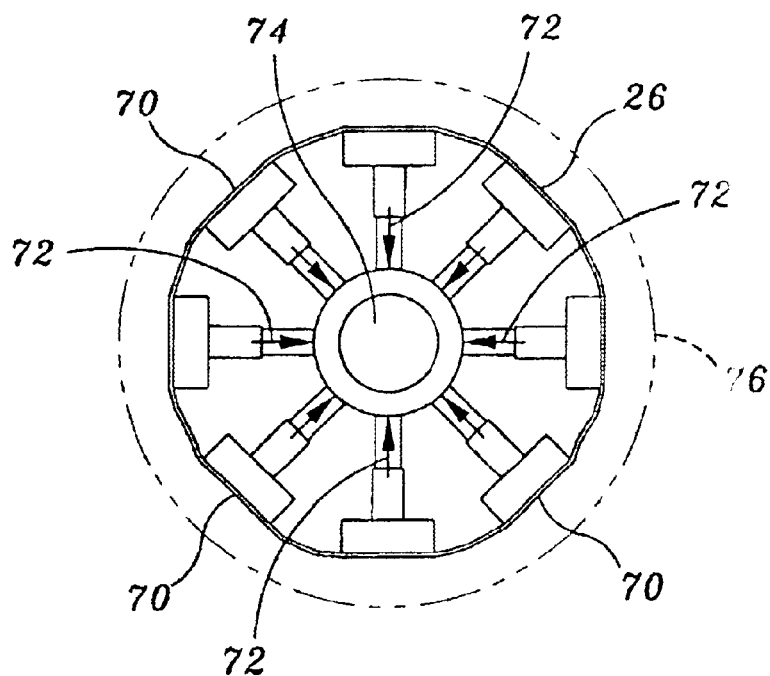
FIG. 13 is a cross-sectional view of the tissue expander depicted in FIG. 12 shown assuming a second, constricted configuration wherein the distraction mechanisms are operative to retract radially inward within the encapsulated body mass.

In yet a further embodiment depicted in FIGS. 12 and 13, there is shown a tissue expander of the present invention operative to facilitate the growth of skin and subcutaneous tissue radially inward about a common focal point 74. As illustrated in FIG. 12, the tissue expander is shown in a geometrically expansive configuration wherein a plurality of distraction mechanisms 70 are operative to collectively impart inwardly-oriented radially compressive forces 72. As such, the tissue expander is operative to contract in size, as illustrated in FIG. 13, such that the tissue expander assumes a smaller diameter as compared to the originally-sized diameter (reflected in phantom 76). Accordingly, the tissue expander of the present invention, although primarily operative to form an increase in surface area about which skin and subcutaneous tissue can grow about, can also actually constrict in size and, to the extent tissue is adequately secured about the periphery of encapsulated covering 26, can thus facilitate the growth of tissue by shrinking, rather than expanding. As will again be appreciated, such ability of prior art tissue expanders to facilitate of growth of skin and subcutaneous tissue has not heretofore been available.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

I claim:

1. A method for facilitating the expansion of skin and subcutaneous tissue comprising the steps:
    a) implanting a tissue expander beneath a target locus of skin and subcutaneous tissue sought to be expanded, said tissue expander comprising:
        an encapsulated body mass formed from elastic material, said encapsulated body mass defining an enclosed cavity therein;
        a distraction mechanism disposed within said enclosed cavity of said encapsulated body mass, said distraction mechanism being operatively transitional between:
            i) a first neutral configuration wherein said distraction mechanism assumes a compact state and exerts a baseline amount of pressure from within said enclosed cavity; and
            ii) a second operative configuration wherein said distraction mechanism exerts an outwardly expansive force operative to increase the external surface area of said encapsulated cavity; and
        an actuator disposed within said enclosed cavity and coupled to said distraction mechanism for selectively controlling said distraction mechanism to transition between said neutral operative configurations, said actuator being operable within said enclosed cavity of said encapsulated body mass, said actuator having a signal receiving mechanism formed thereon for receiving remote command signals to control the separation thereof; and a remotely controlled command signal generator operative to generate and transmit command signals to said signal receiving mechanism of said actuator, said command signals being operative to selectively control the degree of pressure exerted by said distraction mechanism as selectively controlled by said actuator;

b) externally actuating said actuator of said tissue expander such that said distraction mechanism of said tissue expander is caused to transition from said neutral configuration to said operative configuration.

2. The method of claim 1 wherein in step b), said actuator is actuated a multiplicity of times over a pre-datermined duration.

3. The method of claim 2 further comprising the steps:

a) maintaining said tissue expander in said expanded state for a duration sufficient to facilitate the growth of skin and subcutaneous tissue; and b) collapsing said tissue expander and removing said tissue expander from said patient.

4. The method of claim 1 wherein in step a), said tissue expander is implanted beneath a target locus of muscle.

* * * * *